United States Patent
Godwin et al.

(10) Patent No.: US 9,624,519 B2
(45) Date of Patent: Apr. 18, 2017

(54) SYSTEM AND METHOD FOR NUCLEIC ACID AMPLIFICATION

(71) Applicant: 454 Life Sciences Corporation, Branford, CT (US)

(72) Inventors: Brian Christopher Godwin, North Haven, CT (US); Priya Shanbhag, Rocky Hill, CT (US); Craig Elder Mealmaker, Jersey City, NJ (US); Gianni Calogero Ferreri, Northford, CT (US); Melinda Palmer, Hamden, CT (US); Shally Hsueh-Wen Wang, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 266 days.

(21) Appl. No.: 14/466,063

(22) Filed: Aug. 22, 2014

(65) Prior Publication Data
US 2015/0056662 A1 Feb. 26, 2015

Related U.S. Application Data

(60) Provisional application No. 61/869,205, filed on Aug. 23, 2013.

(51) Int. Cl.
C12Q 1/68 (2006.01)
C12P 19/34 (2006.01)

(52) U.S. Cl.
CPC .......... *C12P 19/34* (2013.01); *C12Q 1/6837* (2013.01); *C12Q 1/6844* (2013.01); *C12Q 1/6853* (2013.01); *C12Q 1/6869* (2013.01); *C12Q 2525/191* (2013.01); *C12Q 2565/518* (2013.01)

(58) Field of Classification Search
None
See application file for complete search history.

(56) References Cited

U.S. PATENT DOCUMENTS

| | | | |
|---|---|---|---|
| 5,928,905 A | 7/1999 | Stemmer et al. | |
| 6,210,891 B1 | 4/2001 | Nyren et al. | |
| 6,258,568 B1 | 7/2001 | Nyren | |
| 6,274,320 B1 | 8/2001 | Rothberg et al. | |
| 6,828,100 B1 | 12/2004 | Ronaghi | |
| 7,211,390 B2 | 5/2007 | Rothberg et al. | |
| 7,323,305 B2 | 1/2008 | Leamon et al. | |
| 7,575,865 B2 | 8/2009 | Leamon et al. | |
| 7,601,499 B2 | 10/2009 | Berka et al. | |
| 7,622,280 B2 | 11/2009 | Holliger et al. | |
| 7,638,276 B2 | 12/2009 | Griffiths et al. | |
| 7,682,816 B2 | 3/2010 | Kim et al. | |
| 7,842,457 B2 | 11/2010 | Berka et al. | |
| 7,888,034 B2 | 2/2011 | Simen et al. | |
| 7,927,797 B2 | 4/2011 | Nobile et al. | |
| 8,012,690 B2 | 9/2011 | Berka et al. | |
| 8,301,394 B2 | 10/2012 | Chen et al. | |
| 8,364,417 B2 | 1/2013 | Chen et al. | |
| 8,617,816 B2 | 12/2013 | Simen et al. | |
| 2001/0049125 A1* | 12/2001 | Stemmer ................ C12N 15/10 435/91.1 |
| 2004/0185484 A1 | 9/2004 | Costa | |
| 2004/0248161 A1 | 12/2004 | Rothenberg et al. | |
| 2006/0228721 A1 | 10/2006 | Leamon | |
| 2008/0242560 A1* | 10/2008 | Gunderson .......... B01J 19/0046 506/26 |
| 2008/0318796 A1* | 12/2008 | Drmanac ............. C12Q 1/6809 506/3 |
| 2009/0018024 A1* | 1/2009 | Church ................ C12Q 1/6874 506/2 |
| 2009/0036325 A1* | 2/2009 | McKernan ........... C12Q 1/6806 506/26 |
| 2009/0053724 A1 | 2/2009 | Roth et al. | |
| 2009/0105959 A1 | 4/2009 | Braverman | |
| 2009/0203086 A1 | 8/2009 | Chen et al. | |

(Continued)

FOREIGN PATENT DOCUMENTS

| EP | 14181036 | 1/2015 |
| WO | WO9918241 A1 | 4/1994 |
| WO | WO2004013354 A1 | 2/2004 |
| WO | 2008115427 A3 | 11/2008 |

OTHER PUBLICATIONS

Merrifield, R. "Solid Phase Peptide Synthesis. III. An Improved Synthesis of Bradykinin", *Biochemistry*, Sep. 1964, vol. 3, No. 9, p. 1385-1390.
DeAngelis, Margaret M. et al: Solid-Phase Reversible Immobilization for the Isolation of PCR Products. Nucleic Acids Res (1995), vol. 23:22; 4742-4743.
Sharbati-Tehrani, Soroush, et al., 2008, "Concatameric Cloning of Porcine MicroRNA Molecules after Assembly PCR", Biochemical and Biophysical Research Communications, 375:484-489.

*Primary Examiner* — Aaron Priest
(74) *Attorney, Agent, or Firm* — Cooley LLP; Ivor R. Elrifi; Christina K. Stock

(57) ABSTRACT

An embodiment of a method for generating a population of amplified concatamer products is described that comprises amplifying a template nucleic acid molecule using a first nucleic acid primer immobilized on a bead substrate and a second nucleic acid primer in solution to generate a population of substantially identical copies of the template nucleic acid molecule immobilized on the bead substrate; and amplifying the population of substantially identical copies of the template nucleic acid molecule using a concatamer primer that comprises a first region complementary to an end region of the population of substantially identical copies of the template nucleic acid molecule and a second region to generate a population of immobilized concatamer products of the substantially identical copies of the template nucleic acid molecule.

18 Claims, 10 Drawing Sheets

(56) References Cited

U.S. PATENT DOCUMENTS

| | | |
|---|---|---|
| 2009/0233291 A1 | 9/2009 | Chen et al. |
| 2010/0136516 A1 | 6/2010 | Simen et al. |
| 2011/0003701 A1 | 1/2011 | Ferreri et al. |
| 2011/0177587 A1 | 7/2011 | Nobile et al. |
| 2011/0201526 A1 | 8/2011 | Berka |
| 2013/0217023 A1* | 8/2013 | Godwin ............... C12Q 1/6874 435/6.12 |

* cited by examiner

Standard PCR results in a hard stop in sequencing at the end of the template

When the reaction begins to read into the next sequencing primer the flowgram shows a weaker match

SYSTEM AND METHOD FOR NUCLEIC ACID AMPLIFICATION

CROSS-REFERENCE TO RELATED APPLICATIONS

This application is related to and claims priority from U.S. Provisional Patent Application Ser. No. 61/869,205, titled "System and Method for Nucleic Acid Amplification", filed Aug. 23, 2013, the contents of which is herein incorporated by reference in its entirety.

FIELD OF THE INVENTION

The present invention relates to the fields of nucleic acid amplification. More specifically, the invention relates to systems and methods for increasing the amplification yield of nucleic acid templates via concatamerization.

INCORPORATION BY REFERENCE OF SEQUENCE LISTING

The contents of the text file named "454L-058-001US_ST25.txt", which was created on Nov. 7, 2016 and is 6 KB in size, are hereby incorporated by reference in their entireties.

BACKGROUND OF THE INVENTION

Clonal amplification of nucleic acid template molecules has proven to be very useful for a number of technologies, particularly for nucleic acid sequencing technologies where clonal populations of substantially identical copies amplified from a single template are immobilized on to a solid phase surface and utilized in subsequent sequencing operations. For example, a solid phase surface may comprise an independent solid phase surface (generally referred to as a "bead" substrate although such substrates are not necessarily spherical) that may be disposed in wells. The solid phase surface may also comprise other planar or non-planar surfaces and are used for immobilization and sequencing of clonal populations of amplified nucleic acid template. Typically, a species of amplification primer is disposed on the outer surface of the solid phase which may include surface within pores or cavities (i.e. in the case of a porous bead substrate) or within defined areas of a substrate surface (i.e. in the case of planar substrates that comprise many areas or "features" for amplification of individual template species of various possible shapes and sizes) in order to allow for parallel processing of many different template species.

Thus in many cases there are spatial limitations on the amount of surface area available as primer attachment sites and thus by extension on the amount of amplification product than can be bound to the solid phase substrate. For example, using common PCR reaction conditions, the total amount of nucleic acid template that can be amplified is capped by the total number of primers attached to the surface leading to a maximum 1:1 ratio of amplified nucleic acid template to primers. This can be problematic for downstream applications such as sequencing because the degree of signal obtainable from the population is proportional to the number of copies available to generate the signal where small numbers of copies may not generate enough signal to distinguish from experimental or background noise sources.

One solution has been to implement what is generally referred to as a concatamer PCR approach that makes it possible to increase the ratio of amplified nucleic acid template to primers to greater than 1:1. In other words producing more amplified nucleic acid template than there are primer sites on the surface.

To date concatamer PCR has been achieved in a couple of ways. A first approach requires the initial templates to contain tandem repeats of the starting template sequence which allow for self-priming and amplification. A second approach employed includes amplifying initial PCR products with a restriction enzyme site engineered into both ends of the fragments which can be subsequently digested producing "sticky" ends which can then be ligated to form the initial tandem repeat templates. This template would then be used in the concatamer PCR reaction.

The embodiments of the invention as described herein replace the requirement of tandem copies in the initial template of the concatamer PCR by employing a concatamer primer in the reaction and enables solid surface amplification strategies that allow for sequencing of the DNA template or other uses.

A number of references are cited herein, the entire disclosures of which are incorporated herein, in their entirety, by reference for all purposes. Further, none of these references, regardless of how characterized above, is admitted as prior art to the invention of the subject matter claimed herein.

SUMMARY OF THE INVENTION

Embodiments of the invention relate to the fields of nucleic acid amplification and sequencing. More particularly, embodiments of the invention relate to increasing the amplification yield of nucleic acid templates via concatamerization.

An embodiment of a method for generating a population of amplified concatamer products is described that comprises amplifying a template nucleic acid molecule using a first nucleic acid primer immobilized on a solid phase (e.g., bead) substrate and a second nucleic acid primer in solution to generate a population of substantially identical copies of the template nucleic acid molecule immobilized on the solid phase (e.g., bead) substrate; and amplifying the population of substantially identical copies of the template nucleic acid molecule using a concatamer primer that comprises a first region complementary to an end region of the population of substantially identical copies of the template nucleic acid molecule and a second region to generate a population of immobilized concatamer products of the substantially identical copies of the template nucleic acid molecule.

In some embodiments, each of the population of immobilized concatamer products contains two or more concatamer copies of one of the substantially identical copies of the template nucleic acid molecule.

In the methods described herein, the end region of the population of substantially identical copies of the template nucleic acid molecule can include an adaptor region.

The second region of the concatamer primer can be complementary to the first nucleic acid primer immobilized on the solid phase substrate.

In any of the methods described herein, the solid phase substrate can be fabricated from cellulose, a cellulose derivative, an acrylic resin, glass, a silica gel, polystyrene, gelatin, polyvinyl pyrrolidone, a co-polymer of vinyl and acrylamide, a polystyrene cross-linked with divinylbenzene, polyacrylamide, a latex gel, polystyrene, dextran, rubber, silicon, a plastic, nitrocellulose, a natural sponge, a silica gel, control pore glass, a metal, a cross-linked dextran, and/or agarose gel.

In the methods of the instant invention, the template nucleic acid molecule may have a length of up to 1000 nucleic acid residues (i.e., 25-30 nucleic acid residues, 50-100 nucleic acid residues, 200-300 nucleic acid residues, 350-500 nucleic acid residues, or 500-1000 nucleic acid residues).

Additionally, the template nucleic acid molecule may contain one or more additional functional elements selected from a primer sequence for amplification or sequencing methods, a quality control element, an adapter element, and/or a unique identifier. In some embodiments, the unique identifier is a multiplex identifier (MID), which identifies a feature of a sample, wherein the feature is an experimental condition, a treatment, a species, an individual subject, a tissue type, and/or a cell type. In certain embodiments, the template nucleic acid molecule can contain more than one MID. The position of the MID in the template nucleic acid molecule may be known relative to a feature of the template nucleic acid molecule (e.g., a specific nucleic acid residue in the molecule, a recognizable sequence marker such as a Key element, or one or more primer elements) or to an adaptor element coupled to the template molecule. The Key element or the one or more primer element may each have a known sequence composition.

In the methods described herein, amplifying the population of substantially identical copies of the template nucleic acid molecule using a concatamer primer occurs via polymerase chain reaction (PCR) or emulsion PCR (emPCR).

In certain embodiments, the solid phase substrate is a bead. Such beads can have a diameter of between about 1.4 μm and about 20 μm. In other embodiments, the solid phase substrate is a planar substrate selected from a slide type substrate, a semiconductor chip comprising well type structures, a microwell array, a waveguide type reaction substrate, and/or a PTP array.

Also provided are systems for generating a population of amplified concatamer products, comprising a means for performing any of the methods of the invention.

Any of the above aspects and embodiments can be combined with any other aspect or embodiment.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears. All of these conventions, however, are intended to be typical or illustrative, rather than limiting.

DETAILED DESCRIPTION OF THE INVENTION

Figure 1:
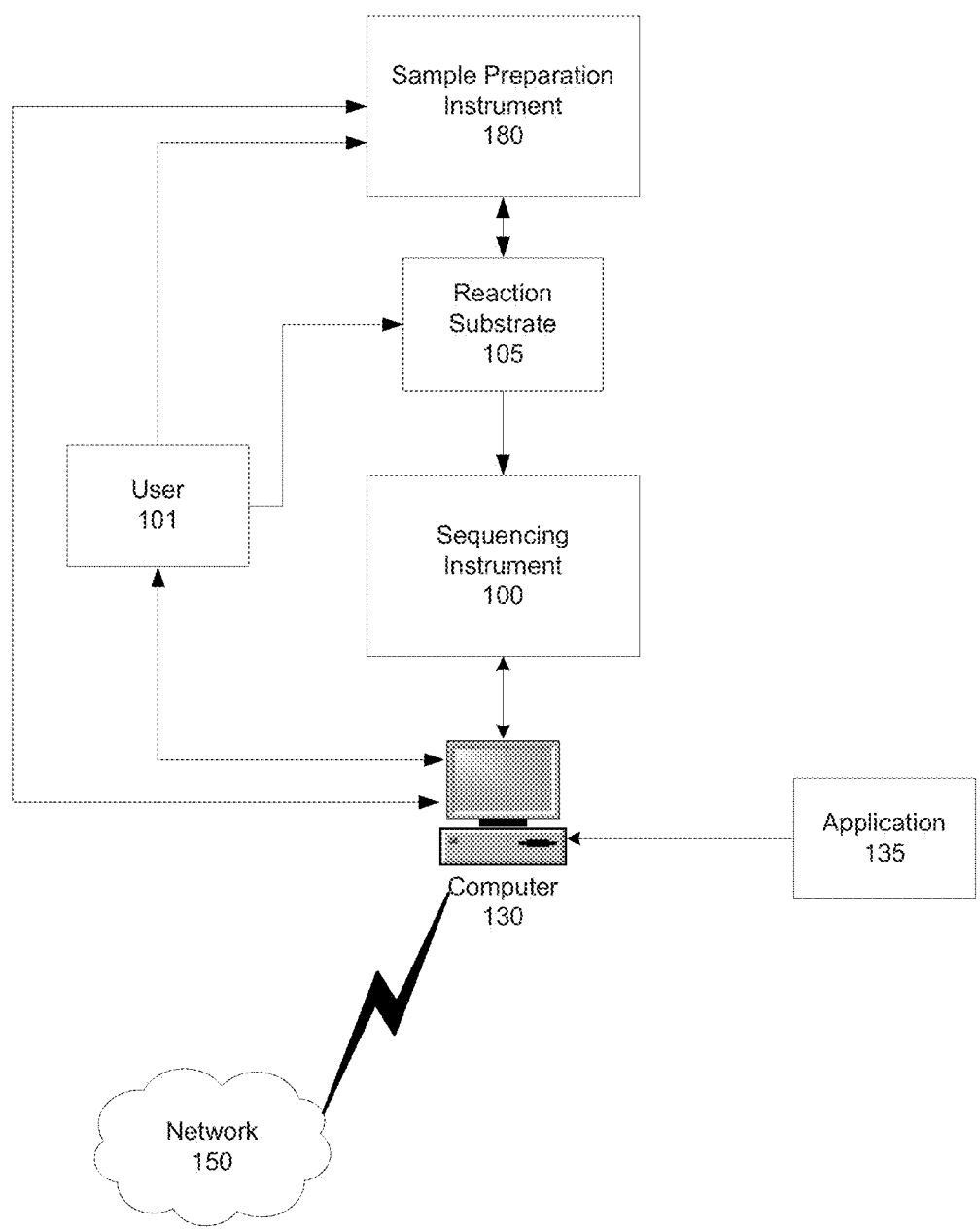
FIG. 1 is a functional block diagram of one embodiment of a sequencing instrument under computer control and a reaction substrate.
Figure 2A:
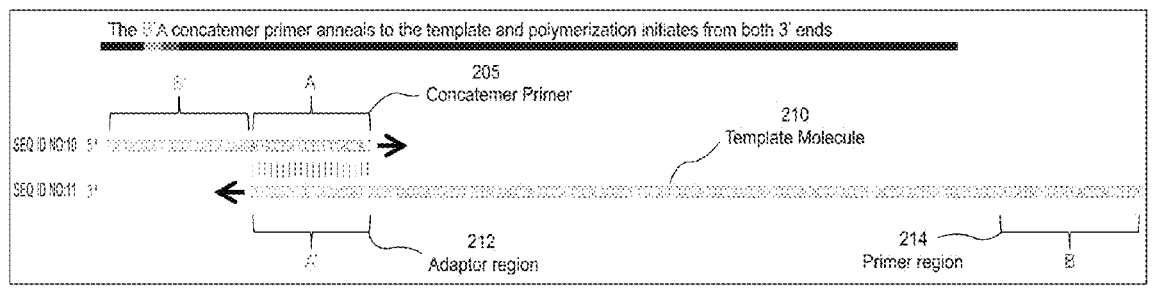
FIGS. 2(A)-(D) are a simplified graphical representation of one embodiment of an amplification strategy using a concatemer primer species.
Figure 2B:
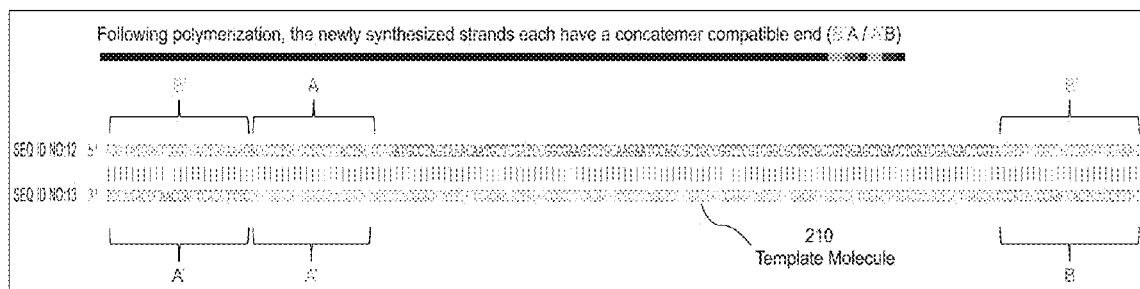
Figure 2C:
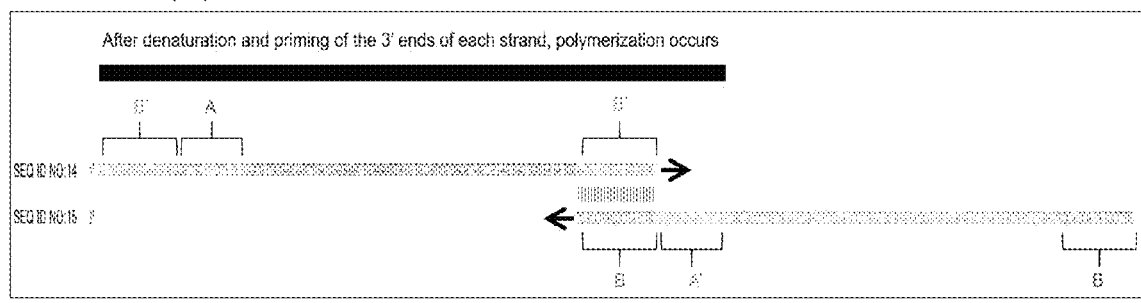
Figure 2D:
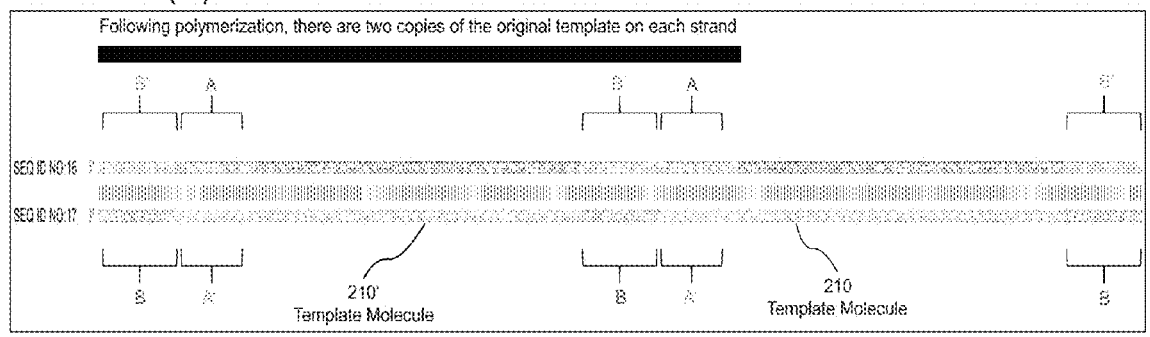

As will be described in greater detail below, embodiments of the presently described invention include systems and methods for increasing the amount of amplification product relative to the number of available primers of a primer species. In the embodiments described in detail below a unique concatamer PCR approach enables the production of a high ratio of amplified DNA copies relative to the amount of primers attached to a surface. The amplified products from concatamer PCR confer a number of advantages for subsequent processing and/or analysis steps. For example, the concatamer PCR products alleviate surface crowding issues due to the fact that the products amplify away from the solid phase surface. Further, inhibition caused by an increase in double stranded DNA ends is reduced because amplification products can be formed without increasing the number of double stranded ends. Lastly, the Concatamer PCR process is less limited by the concentrations of solution phase and solid phase primers due to the fact that the ends regions of the amplification products act as primer sites.

a. General

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents, and other references are incorporated in toto herein by reference. In addition, the materials, methods, and examples are illustrative only and not intended to be limiting.

The term "flowgram" generally refers to a graphical representation of sequence data generated by SBS methods, particularly pyrophosphate based sequencing methods (also referred to as "pyrosequencing") and may be referred to more specifically as a "pyrogram".

The term "read" or "sequence read" as used herein generally refers to the entire sequence data obtained from a single nucleic acid template molecule or a population of a plurality of substantially identical copies of the template nucleic acid molecule.

The terms "run" or "sequencing run" as used herein generally refer to a series of sequencing reactions performed in a sequencing operation of one or more template nucleic acid molecules.

The term "flow" as used herein generally refers to a single introduction of a nucleotide species or reagent into a reaction environment that is typically part of an iterative sequencing by synthesis process comprising a template nucleic acid molecule. For example, a flow may include a solution comprising a nucleotide species and/or one or more other reagents, such as buffers, wash solutions, or enzymes that may be employed in a sequencing process or to reduce carryover or noise effects from previous flows of nucleotide species.

The term "flow order", "flow pattern", or "nucleotide dispensation order" as used herein generally refers to a pre-determined series of flows of a nucleotide species into a reaction environment. In some embodiments a flow cycle may include a sequential addition of 4 nucleotide species in the order of T, A, C, G nucleotide species, or other order where one or more of the nucleotide species may be repeated.

The term "flow cycle" as used herein generally refers to an iteration of a flow order where in some embodiments the flow cycle is a repeating cycle having the same flow order from cycle to cycle, although in some embodiments the flow order may vary from cycle to cycle.

The term "read length" as used herein generally refers to an upper limit of the length of a template molecule that may be reliably sequenced. There are numerous factors that contribute to the read length of a system and/or process including, but not limited to the degree of GC content in a template nucleic acid molecule.

The term "signal droop" as used herein generally refers to a decline in detected signal intensity as read length increases.

The term "test fragment" or "TF" as used herein generally refers to a nucleic acid element of known sequence composition that may be employed for quality control, calibration, or other related purposes.

The term "primer" as used herein generally refers to an oligonucleotide that acts as a point of initiation of DNA synthesis under conditions in which synthesis of a primer extension product complementary to a nucleic acid strand is induced in an appropriate buffer at a suitable temperature. A primer is preferably a single stranded oligodeoxyribonucleotide.

A "nascent molecule" generally refers to a DNA strand which is being extended by the template-dependent DNA polymerase by incorporation of nucleotide species which are complementary to the corresponding nucleotide species in the template molecule.

The terms "template nucleic acid", "template molecule", "target nucleic acid", or "target molecule" generally refer to a nucleic acid molecule that is the subject of a sequencing reaction from which sequence data or information is generated.

The term "nucleotide species" as used herein generally refers to the identity of a nucleic acid monomer including purines (Adenine, Guanine) and pyrimidines (Cytosine, Uracil, Thymine) typically incorporated into a nascent nucleic acid molecule. "Natural" nucleotide species include, e.g., adenine, guanine, cytosine, uracil, and thymine. Modified versions of the above natural nucleotide species include, without limitation, alpha-thio-triphosphate derivatives (such as dATP alpha S), hypoxanthine, xanthine, 7-methylguanine, 5, 6-dihydrouracil, and 5-methylcytosine.

The term "monomer repeat" or "homopolymers" as used herein generally refers to two or more sequence positions comprising the same nucleotide species (i.e. a repeated nucleotide species).

The term "homogeneous extension" as used herein generally refers to the relationship or phase of an extension reaction where each member of a population of substantially identical template molecules is homogenously performing the same extension step in the reaction.

The term "completion efficiency" as used herein generally refers to the percentage of nascent molecules that are properly extended during a given flow.

The term "incomplete extension rate" as used herein generally refers to the ratio of the number of nascent molecules that fail to be properly extended over the number of all nascent molecules.

The term "genomic library" or "shotgun library" as used herein generally refers to a collection of molecules derived from and/or representing an entire genome (i.e. all regions of a genome) of an organism or individual.

The term "amplicon" as used herein generally refers to selected amplification products, such as those produced from Polymerase Chain Reaction (PCR) or Ligase Chain Reaction (LCR) techniques.

The term "variant" or "allele" as used herein generally refers to one of a plurality of species each encoding a similar sequence composition, but with a degree of distinction from each other. The distinction may include any type of variation known to those of ordinary skill in the related art, that include, but are not limited to, polymorphisms such as single nucleotide polymorphisms (SNPs), insertions or deletions (the combination of insertion/deletion events are also referred to as "indels"), differences in the number of repeated sequences (also referred to as tandem repeats), and structural variations.

The term "allele frequency" or "allelic frequency" as used herein generally refers to the proportion of all variants in a population that is comprised of a particular variant.

The term "key sequence" or "key element" as used herein generally refers to a nucleic acid sequence element (typically of about 4 sequence positions, i.e., TGAC or other combination of nucleotide species) associated with a template nucleic acid molecule in a known location (i.e., typically included in a ligated adaptor element) comprising known sequence composition that is employed as a quality control reference for sequence data generated from template molecules. The sequence data passes the quality control if it includes the known sequence composition associated with a Key element in the correct location.

The term "keypass" or "keypass well" as used herein generally refers to the sequencing of a full length nucleic acid test sequence of known sequence composition (i.e., a "test fragment" or "TF" as referred to above) in a reaction well, where the accuracy of the sequence derived from TF sequence and/or Key sequence associated with the TF or in an adaptor associated with a target nucleic acid is compared to the known sequence composition of the TF and/or Key and used to measure of the accuracy of the sequencing and for quality control. In typical embodiments, a proportion of the total number of wells in a sequencing run will be keypass wells which may, in some embodiments, be regionally distributed.

The term "blunt end" as used herein is interpreted consistently with the understanding of one of ordinary skill in the related art, and generally refers to a linear double stranded nucleic acid molecule having an end that terminates with a pair of complementary nucleotide base species, where a pair of blunt ends are typically compatible for ligation to each other.

The term "sticky end" or "overhang" as used herein is interpreted consistently with the understanding of one of ordinary skill in the related art, and generally refers to a linear double stranded nucleic acid molecule having one or more unpaired nucleotide species at the end of one strand of the molecule, where the unpaired nucleotide species may exist on either strand and include a single base position or a plurality of base positions (also sometimes referred to as "cohesive end").

The term "SPRI" as used herein is interpreted consistently with the understanding of one of ordinary skill in the related art, and generally refers to the patented technology of "Solid Phase Reversible Immobilization" wherein target nucleic acids are selectively precipitated under specific buffer conditions in the presence of beads, where said beads are often carboxylated and paramagnetic. The precipitated target nucleic acids immobilize to said beads and remain bound until removed by an elution buffer according to the operator's needs (DeAngelis, Margaret M. et al: Solid-Phase Reversible Immobilization for the Isolation of PCR Products. *Nucleic Acids Res* (1995), Vol. 23:22; 4742-4743, which is hereby incorporated by reference herein in its entirety for all purposes).

The term "carboxylated" as used herein is interpreted consistently with the understanding of one of ordinary skill in the related art, and generally refers to the modification of a material, such as a microparticle, by the addition of at least one carboxl group. A carboxyl group is either COOH or COO—.

The term "paramagnetic" as used herein is interpreted consistently with the understanding of one of ordinary skill in the related art, and generally refers to the characteristic of a material wherein said material's magnetism occurs only in the presence of an external, applied magnetic field and does not retain any of the magnetization once the external, applied magnetic field is removed.

The term "bead" or "bead substrate" as used herein generally refers to any type of solid phase particle of any convenient size, of irregular or regular shape and which is fabricated from any number of known materials such as cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase bead supports known to those of skill in the art although it will be appreciated that solid phase substrates may include a degree of porosity enabling penetration of fluids and/or biological molecule into the pores.

The term "reaction environment" as used herein generally refers to a volume of space in which a reaction can take place typically where reactants are at least temporarily contained or confined allowing for detection of at least one reaction product. Examples of a reaction environment include but are not limited to cuvettes, tubes, bottles, as well as one or more depressions, wells, or chambers on a planar or non-planar substrate.

The term "virtual terminator" as used herein generally refers to terminators substantially slow reaction kinetics where additional steps may be employed to stop the reaction such as the removal of reactants.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Some exemplary embodiments of systems and methods associated with sample preparation and processing, generation of sequence data, and analysis of sequence data are generally described below, some or all of which are amenable for use with embodiments of the presently described invention. In particular, the exemplary embodiments of systems and methods for preparation of template nucleic acid molecules, amplification of template molecules, generating target specific amplicons and/or genomic libraries, sequencing methods and instrumentation, and computer systems are described.

In typical embodiments, the nucleic acid molecules derived from an experimental or diagnostic sample should be prepared and processed from its raw form into template molecules amenable for high throughput sequencing. The processing methods may vary from application to application, resulting in template molecules comprising various characteristics. For example, in some embodiments of high throughput sequencing, it is preferable to generate template molecules with a sequence or read length that is at least comparable to the length that a particular sequencing method can accurately produce sequence data for. In the present example, the length may include a range of about 25-30 bases, about 50-100 bases, about 200-300 bases, about 350-500 bases, about 500-1000 bases, greater than 1000 bases, or any other length amenable for a particular sequencing application. In some embodiments, nucleic acids from a sample, such as a genomic sample, are fragmented using a number of methods known to those of ordinary skill in the art. In preferred embodiments, methods that randomly fragment (i.e. do not select for specific sequences or regions)

nucleic acids and may include what is referred to as nebulization or sonication methods. It will, however, be appreciated that other methods of fragmentation, such as digestion using restriction endonucleases, may be employed for fragmentation purposes. Also in the present example, some processing methods may employ size selection methods known in the art to selectively isolate nucleic acid fragments of the desired length.

Also, it is preferable in some embodiments to associate additional functional elements with each template nucleic acid molecule. The elements may be employed for a variety of functions including, but not limited to, primer sequences for amplification and/or sequencing methods, quality control elements (i.e. such as Key elements or other type of quality control element), unique identifiers (also referred to as a multiplex identifier or "MID") that encode various associations such as with a sample of origin or patient, or other functional element.

For example, some embodiments of the described invention comprise associating one or more embodiments of an MID element having a known and identifiable sequence composition with a sample, and coupling the embodiments of MID element with template nucleic acid molecules from the associated samples. The MID coupled template nucleic acid molecules from a number of different samples are pooled into a single "Multiplexed" sample or composition that can then be efficiently processed to produce sequence data for each MID coupled template nucleic acid molecule. The sequence data for each template nucleic acid is deconvoluted to identify the sequence composition of coupled MID elements and association with sample of origin identified. In the present example, a multiplexed composition may include representatives from about 384 samples, about 96 samples, about 50 samples, about 20 samples, about 16 samples, about 12 samples, about 10 samples, or other number of samples. Each sample may be associated with a different experimental condition, treatment, species, or individual in a research context. Similarly, each sample may be associated with a different tissue, cell, individual, condition, drug or other treatment in a diagnostic context. Those of ordinary skill in the related art will appreciate that the numbers of samples listed above are provided for exemplary purposes and thus should not be considered limiting.

In preferred embodiments, the sequence composition of each MID element is easily identifiable and resistant to introduced error from sequencing processes. Some embodiments of MID element comprise a unique sequence composition of nucleic acid species that has minimal sequence similarity to a naturally occurring sequence. Alternatively, embodiments of a MID element may include some degree of sequence similarity to naturally occurring sequence.

Also, in preferred embodiments, the position of each MID element is known relative to some feature of the template nucleic acid molecule and/or adaptor elements coupled to the template molecule. Having a known position of each MID is useful for finding the MID element in sequence data and interpretation of the MID sequence composition for possible errors and subsequent association with the sample of origin.

For example, some features useful as anchors for positional relationship to MID elements may include, but are not limited to, the length of the template molecule (i.e. the MID element is known to be so many sequence positions from the 5' or 3' end), recognizable sequence markers such as a Key element and/or one or more primer elements positioned adjacent to a MID element. In the present example, the Key and primer elements generally comprise a known sequence composition that typically does not vary from sample to sample in the multiplex composition and may be employed as positional references for searching for the MID element. An analysis algorithm implemented by application 135 may be executed on computer 130 to analyze generated sequence data for each MID coupled template to identify the more easily recognizable Key and/or primer elements, and extrapolate from those positions to identify a sequence region presumed to include the sequence of the MID element. Application 135 may then process the sequence composition of the presumed region and possibly some distance away in the flanking regions to positively identify the MID element and its sequence composition.

Some or all of the described functional elements may be combined into adaptor elements that are coupled to nucleotide sequences in certain processing steps. For example, some embodiments may associate priming sequence elements or regions comprising complementary sequence composition to primer sequences employed for amplification and/or sequencing. Further, the same elements may be employed for what may be referred to as "strand selection" and immobilization of nucleic acid molecules to a solid phase substrate. In some embodiments, two sets of priming sequence regions (hereafter referred to as priming sequence A, and priming sequence B) may be employed for strand selection, where only single strands having one copy of priming sequence A and one copy of priming sequence B is selected and included as the prepared sample. In alternative embodiments, design characteristics of the adaptor elements eliminate the need for strand selection. The same priming sequence regions may be employed in methods for amplification and immobilization where, for instance, priming sequence B may be immobilized upon a solid substrate and amplified products are extended therefrom.

Additional examples of sample processing for fragmentation, strand selection, and addition of functional elements and adaptors are described in U.S. Publication No. 2004-0185484, titled "Method for preparing single-stranded DNA libraries", filed Jan. 28, 2004; U.S. Publication No. 2009-0105959, titled "System and Method for Identification of Individual Samples from a Multiplex Mixture", filed May 29, 2008; and U.S. Publication No. 2011-0003701, titled "System and Method for Improved Processing of Nucleic Acids for Production of Sequencable Libraries", filed Feb. 23, 2009, each of which is hereby incorporated by reference herein in its entirety for all purposes.

Various examples of systems and methods for performing amplification of template nucleic acid molecules to generate populations of substantially identical copies are described. It will be apparent to those of ordinary skill that it is desirable in some embodiments of SBS to generate many copies of each nucleic acid element to generate a stronger signal when one or more nucleotide species is incorporated into each nascent molecule associated with a copy of the template molecule. There are many techniques known in the art for generating copies of nucleic acid molecules such as, for instance, amplification using what are referred to as bacterial vectors, "Rolling Circle" amplification (described in U.S. Pat. Nos. 6,274,320 and 7,211,390, incorporated by reference above) and Polymerase Chain Reaction (PCR) methods, each of the techniques are applicable for use with the presently described invention. One PCR technique that is particularly amenable to high throughput applications include what are referred to as emulsion PCR methods (also referred to as emPCR methods).

Typical embodiments of emulsion PCR methods include creating a stable emulsion of two immiscible substances creating aqueous droplets within which reactions may occur. In particular, the aqueous droplets of an emulsion amenable for use in PCR methods may include a first fluid, such as a water based fluid suspended or dispersed as droplets (also referred to as a discontinuous phase) within another fluid, such as a hydrophobic fluid (also referred to as a continuous phase) that typically includes some type of oil. Examples of oil that may be employed include, but are not limited to, mineral oils, silicone based oils, or fluorinated oils.

Further, some emulsion embodiments may employ surfactants that act to stabilize the emulsion, which may be particularly useful for specific processing methods such as PCR. Some embodiments of surfactant may include one or more of a silicone or fluorinated surfactant. For example, one or more non-ionic surfactants may be employed that include, but are not limited to, sorbitan monooleate (also referred to as Span® 80, Sigma-Aldrich, USA), polyoxyethylenesorbitsan monooleate (also referred to as Tween® 80, Sigma-Aldrich, USA), or in some preferred embodiments, dimethicone copolyol (also referred to as Abil® EM90), polysiloxane, polyalkyl polyether copolymer, polyglycerol esters, poloxamers, and PVP/hexadecane copolymers (also referred to as Unimer U-151), or in more preferred embodiments, a high molecular weight silicone polyether in cyclopentasiloxane (also referred to as Dow Corning® 5225C available from Dow Corning).

The droplets of an emulsion may also be referred to as compartments, microcapsules, microreactors, microenvironments, or other name commonly used in the related art. The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agent may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate such as a bead for attachment of template and amplified copies of the template, amplified copies complementary to the template, or combination thereof. Further, the solid substrate may be enabled for attachment of other type of nucleic acids, reagents, labels, or other molecules of interest.

After emulsion breaking and bead recovery, it may also be desirable in typical embodiments to "enrich" for beads having a successfully amplified population of substantially identical copies of a template nucleic acid molecule immobilized thereon. For example, a process for enriching for "DNA positive" beads may include hybridizing a primer species to a region on the free ends of the immobilized amplified copies, typically found in an adaptor sequence, extending the primer using a polymerase mediated extension reaction, and binding the primer to an enrichment substrate such as a magnetic or sepharose bead. A selective condition may be applied to the solution comprising the beads, such as a magnetic field or centrifugation, where the enrichment bead is responsive to the selective condition and is separated from the "DNA negative" beads (i.e. NO: or few immobilized copies).

Embodiments of an emulsion useful with the presently described invention may include a very high density of droplets or microcapsules enabling the described chemical reactions to be performed in a massively parallel way. Additional examples of emulsions employed for amplification and their uses for sequencing applications are described in U.S. Pat. Nos. 7,638,276; 7,622,280; 7,842,457; 7,927,797; and 8,012,690 and U.S. Patent Publication No. 2011-0201526, each of which is hereby incorporated by reference herein in its entirety for all purposes.

Also embodiments sometimes referred to as Ultra-Deep Sequencing, generate target specific amplicons for sequencing may be employed with the presently described invention that include using sets of specific nucleic acid primers to amplify a selected target region or regions from a sample comprising the target nucleic acid. Further, the sample may include a population of nucleic acid molecules that are known or suspected to contain sequence variants comprising sequence composition associated with a research or diagnostic utility where the primers may be employed to amplify and provide insight into the distribution of sequence variants in the sample. For example, a method for identifying a sequence variant by specific amplification and sequencing of multiple alleles in a nucleic acid sample may be performed. The nucleic acid is first subjected to amplification by a pair of PCR primers designed to amplify a region surrounding the region of interest or segment common to the nucleic acid population. Each of the products of the PCR reaction (first amplicons) is subsequently further amplified individually in separate reaction vessels such as an emulsion based vessel described above. The resulting amplicons (referred to herein as second amplicons), each derived from one member of the first population of amplicons, are sequenced and the collection of sequences are used to determine an allelic frequency of one or more variants present. Importantly, the method does not require previous knowledge of the variants present and can typically identify variants present at <1% frequency in the population of nucleic acid molecules.

Some advantages of the described target specific amplification and sequencing methods include a higher level of sensitivity than previously achieved and are particularly useful for strategies comprising mixed populations of template nucleic acid molecules. Further, embodiments that employ high throughput sequencing instrumentation, such as for instance embodiments that employ what is referred to as a PicoTiterPlate array (also sometimes referred to as a PTP plate or array) of wells provided by 454 Life Sciences Corporation, the described methods can be employed to generate sequence composition for over 100,000, over 300,000, over 500,000, or over 1,000,000 nucleic acid regions per run or experiment and may depend, at least in part, on user preferences such as lane configurations enabled by the use of gaskets, etc. Also, the described methods provide a sensitivity of detection of low abundance alleles which may represent 1% or less of the allelic variants present in a sample. Another advantage of the methods includes generating data comprising the sequence of the analyzed region. Importantly, it is not necessary to have prior knowledge of the sequence of the locus being analyzed.

Additional examples of target specific amplicons for sequencing are described in U.S. Publication No. 2006-0228721, titled "Methods for determining sequence variants using ultra-deep sequencing", filed Apr. 12, 2005; PCT Publication WO 2008115427, titled "System and Method for Detection of HIV Drug Resistant Variants", filed Mar. 14, 2008, which was patented in the United States as U.S. Pat. No. 8,617,816 on Dec. 13, 2013; and U.S. Pat. No. 7,888,034, titled "System and Method for Detection of HIV Tropism Variants", filed Jun. 17, 2009; and US Publication No. 2010-0136516, titled "System and Method for Detection of HIV Integrase Variants", filed Nov. 19, 2009, each of which is hereby incorporated by reference herein in its entirety for all purposes.

Further, embodiments of sequencing may include Sanger type techniques, techniques generally referred to as Sequencing by Hybridization (SBH), Sequencing by Ligation (SBL), or Sequencing by Incorporation (SBI) techniques. The sequencing techniques may also include what are referred to as polony sequencing techniques; nanopore, waveguide and other single molecule detection techniques; or reversible terminator techniques. As described above, a preferred technique may include Sequencing by Synthesis methods. For example, some SBS embodiments sequence populations of substantially identical copies of a nucleic acid template and typically employ one or more oligonucleotide primers designed to anneal to a predetermined, complementary position of the sample template molecule or one or more adaptors attached to the template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide species that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. It will also be appreciated that the process of adding a nucleotide species to the end of a nascent molecule is substantially the same as that described above for addition to the end of a primer.

As described above, incorporation of the nucleotide species can be detected by a variety of methods known in the art, e.g. by detecting the release of pyrophosphate (PPi) using an enzymatic reaction process to produce light or via detection the release of H$^+$ and measurement of pH change (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include, but are not limited to, mass tags and fluorescent or chemiluminescent labels. In typical embodiments, unincorporated nucleotides are removed, for example by washing. Further, in some embodiments, the unincorporated nucleotides may be subjected to enzymatic degradation such as, for instance, degradation using the apyrase or pyrophosphatase enzymes as described in U.S. Publication No. 2009-0053724, titled "System and Method for Adaptive Reagent Control in Nucleic Acid Sequencing", filed Jun. 27, 2008; and U.S. Publication No. 2009-0203086, titled "System and Method for Improved Signal Detection in Nucleic Acid Sequencing", filed Jan. 29, 2009; each of which is hereby incorporated by reference herein in its entirety for all purposes.

In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, extension, signal acquisition, and washing result in a determination of the nucleotide sequence of the template strand. Continuing with the present example, a large number or population of substantially identical template molecules (e.g. $10^3$, $10^4$, $10^5$, $10^6$ or $10^7$ molecules) are typically analyzed simultaneously in any one sequencing reaction, in order to achieve a signal which is strong enough for reliable detection.

In addition, it may be advantageous in some embodiments to improve the read length capabilities and qualities of a sequencing process by employing what may be referred to as a "paired-end" sequencing strategy. For example, some embodiments of sequencing method have limitations on the total length of molecule from which a high quality and reliable read may be generated. In other words, the total number of sequence positions for a reliable read length may not exceed 25, 50, 100, or 500 bases depending on the sequencing embodiment employed. A paired-end sequencing strategy extends reliable read length by separately sequencing each end of a molecule (sometimes referred to as a "tag" end) that comprise a fragment of an original template nucleic acid molecule at each end joined in the center by a linker sequence. The original positional relationship of the template fragments is known and thus the data from the sequence reads may be re-combined into a single read having a longer high quality read length. Further examples of paired-end sequencing embodiments are described in U.S. Pat. No. 7,601,499, titled "Paired end sequencing"; and in U.S. Publication No. 2009-0233291, titled "Paired end sequencing", filed Jan. 28, 2009, each of which is hereby incorporated by reference herein in its entirety for all purposes.

Some examples of SBS apparatus may implement some or all of the methods described above and may include one or more of a detection device such as a charge coupled device (i.e., CCD camera), complementary metal oxide semiconductor (CMOS), or confocal type architecture for optical detection, Ion-Sensitive Field Effect Transistor (also referred to as "ISFET") or Chemical-Sensitive Field Effect Transistor (also referred to as "ChemFET") for architectures for ion or chemical detection, a microfluidics chamber or flow cell, a reaction substrate, and/or a pump and flow valves. Taking the example of pyrophosphate-based sequencing, some embodiments of an apparatus may employ a chemiluminescent detection strategy that produces an inherently low level of background noise.

In some embodiments, the reaction substrate for sequencing may include a planar substrate, such as a slide type substrate, a semiconductor chip comprising well type structures with ISFET detection elements contained therein, or waveguide type reaction substrate that in some embodiments may comprise well type structures. Further, the reaction substrate may include what is referred to as a PTP array available from 454 Life Sciences Corporation, as described above, formed from a fiber optic faceplate that is acid-etched to yield hundreds of thousands or more of very small wells each enabled to hold a population of substantially identical template molecules (i.e., some preferred embodiments comprise about 3.3 million wells on a 70×75 mm PTP array at a 35 μm well to well pitch). In some embodiments, each population of substantially identical template molecule may be disposed upon a solid substrate, such as a bead, each of which may be disposed in one of said wells. For example, an apparatus may include a reagent delivery element for providing fluid reagents to the PTP plate holders, as well as a CCD type detection device enabled to collect photons of light emitted from each well on the PTP plate. An example of reaction substrates comprising characteristics for improved signal recognition is described in U.S. Pat. No. 7,682,816, titled "Thin-Film Coated Microwell Arrays and Methods of Making Same", filed Aug. 30, 2005, which is hereby incorporated by reference herein in its entirety for all purposes. Further examples of apparatus and methods for performing SBS type sequencing and pyrophosphate sequencing are described in U.S. Pat. Nos. 7,323,305 and 7,575,865, both of which are incorporated by reference above.

In addition, systems and methods may be employed that automate one or more sample preparation processes, such as the emPCR process described above. For example, automated systems may be employed to provide an efficient solution for generating an emulsion for emPCR processing, performing PCR Thermocycling operations, and enriching for successfully prepared populations of nucleic acid molecules for sequencing. Examples of automated sample preparation systems are described in U.S. Pat. No. 7,927,797; and U.S. Publication No. 2011-0177587, each of which is hereby incorporated by reference herein in its entirety for all purposes.

Also, the systems and methods of the presently described embodiments of the invention may include implementation of some design, analysis, or other operation using a computer readable medium stored for execution on a computer system. For example, several embodiments are described in detail below to process detected signals and/or analyze data generated using SBS systems and methods where the processing and analysis embodiments are implementable on computer systems.

In some embodiments a data processing application includes algorithms for correcting raw sequence data for the accumulations of CAFIE error. For example, some or all of the CAFIE error factors may be accurately approximated and applied to a theoretical flowgram model to provide a representation of real data obtained from an actual sequencing run and subsequently approximate a theoretical flowgram from an observed flowgram using an inversion of a mathematical model. Thus, an approximation of error may be applied to actual sequencing data represented in an observed flowgram to produce a theoretical flowgram representing the sequence composition of a target nucleic acid with all or substantially all of the error factors removed. Additional examples of CAFIE correction embodiments are described in U.S. Pat. Nos. 8,301,394; and 8,364,417, each of which are hereby incorporated by reference herein in its entirety for all purposes.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows-type operating system (such as Windows XP, Windows Vista, or Windows 7) from the Microsoft Corporation; the Mac OS X operating system from Apple Computer Corp. (such as Mac OS X v10.6 "Snow Leopard" operating systems); a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also, a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

b. Embodiments of the Presently-Described Invention

As described above, the described invention relates to a system and method for increasing the amount of amplification product relative to the number of available primers of a primer species by employing a unique Concatamer PCR approach that enables the production of a high ratio of amplified DNA copies relative to the amount of primers attached to a surface. In embodiments described below, specialized "concatamer primer" species initiate concatenation of a template DNA molecule in a first or early rounds of a PCR type amplification reaction that self-perpetuates without the need for the concatamer primer species in subsequent rounds. It will also be appreciated that in some embodiments isothermal methods such as helicase dependent amplification, recombinase polymerase amplification, G-quadruplex amplification, "Wildfire" amplification and other unidentified methods that produce PCR like products may be able to take advantage of this concatamer method. In particular the design of the concatamer primer species alleviates the need to design self-priming regions into the sequence composition of the template DNA molecule. The amplification products from the concatamer PCR process described herein are particularly useful for nucleic acid sequencing embodiments.

In a typical sequencing embodiment, one or more instrument elements may be employed that automate one or more process steps. For example, embodiments of a sequencing method may be executed using instrumentation to automate and carry out some or all process steps. FIG. 1 provides an illustrative example of sequencing instrument 100 constructed and arranged for sequencing processes requiring capture of signals from one or more embodiments of substrate 105. In some embodiments, reaction substrate 105 comprises a plurality of Ion Sensitive Field Effect Transistors (often referred to as ISFET). Also in the same or alternative embodiments, sequencing instrument 100 comprises a subsystem that operatively couples with substrate 105 with one or more data processing elements, and a fluidic subsystem that enables execution of sequencing reactions on reaction substrate 105. It will, however, be appreciated that for sequencing processes requiring other modes of data capture (i.e. temperature, electric current, electrochemical, etc.), a subsystem for the mode of data capture may be employed which are known to those of ordinary skill in the related art. For instance, a sample of template molecules may be loaded onto reaction substrate 105 by user 101 or some automated embodiment, then sequenced in a massively parallel manner using sequencing instrument 100 to produce sequence data representing the sequence composition of each template nucleic acid molecule. Importantly, user 101 may include any type of user of sequencing technologies.

In some embodiments, samples may be optionally prepared for sequencing in a fully automated or partially automated fashion using sample preparation instrument 180 configured to perform some or all of the necessary sample preparation steps for sequencing using instrument 100. Those of ordinary skill in the art will appreciate that sample preparation instrument 180 is provided for the purposes of illustration and may represent one or more instruments each designed to carry out some or all of the steps associated with sample preparation required for a particular sequencing assay. Examples of sample preparation instruments may include robotic and/or microfluidic platforms such as those available from Hamilton Robotics, Fluidigm Corporation, Beckman Coulter, Agilent Technologies, or Caliper Life Sciences.

Further, as illustrated in FIG. 1, sequencing instrument 100 may be operatively linked to one or more external computer components, such as computer 130 that may, for instance, execute system software or firmware, such as application 135 that may provide instructional control of one or more of the instruments, such as sequencing instrument 100 or sample preparation instrument 180, and/or signal processing/data analysis functions. Computer 130 may be additionally operatively connected to other computers or servers via network 150 that may enable remote operation of instrument systems and the export of large amounts of data to systems capable of storage and processing. Also in some embodiments network 150 may enable what is referred to as "cloud computing" for signal processing and/or data analysis functions. In the present example, sequencing instrument 100 and/or computer 130 may include some or all of the components and characteristics of the embodiments generally described herein.

An embodiment of the concatamer PCR process using an embodiment of concatamer primer species is graphically illustrated in FIG. 2. For example, panel (A) of FIG. 2 includes an embodiment of concatamer primer 205 that comprises a first region and a second region (illustrated as A and B' respectively) where the first region is complementary to a region associated with template molecule 210. In some embodiments the region complementary to concatamer primer 205 includes a region of an adaptor sequence, such as adaptor 212 region. Additional examples of sample processing, strand selection, and addition of functional elements and adaptors are described above.

It will also be appreciated that in some embodiments standard PCR primers may also be employed to perform some function, such as for instance to immobilization of a template molecule to a bead substrate and extension of a first immobilized copy that concatamer primer 205 may then hybridize to. This process could include the immobilization of thousands or millions of substantially identical copies of a template molecule on the bead at about a one to one ratio of copies to the number of immobilized primers on the bead. In the described embodiments there may be one primer species (i.e. an A primer) in solution and a second primer species (i.e. a B primer) immobilized on the bead substrate. For instance, in the example of FIG. 2 template molecule 210 may represent a complementary extension product from the bead substrate. In the described example primer 214 (i.e. a B primer) is immobilized on the bead surface that hybridized to a complementary B' region of an adaptor ligated to an original template molecule that may include a fragment from a larger molecule or an amplification product.

Panel (B) of FIG. 2 illustrates the result of polymerase extension products from concatamer primer 205 that includes a complementary copy of template molecule 210 as well as a new B region that is a complement to the second (B') region of concatamer primer 205. Panel (C) illustrates the result of denaturation of the strands in panel (B) and re-hybridization of the newly synthesized B' region to the newly synthesized B region to the end of template molecule 210. It will be appreciated, however, that some percentage of molecules will re-hybridize to the original complement.

Panel (D) of FIG. 2 then illustrates the result of polymerase extension from the re-hybridized product in panel (C) that illustrates a concatamer comprising template molecule 210 and a first copy, template molecule 210'.

It is important to note that some embodiments of polymerase enzymes may performed better than others in the described concatamer amplification embodiments. For example, an embodiment of deep vent polymerase provided a superior result than other polymerase enzymes both from a yield and specificity standpoint. In general embodiments of polymerase enzymes that lack a 5' to 3' exonuclease activity perform better than embodiments of taq polymerase that retains its 5' to 3' exonuclease activity.

Figure 3:
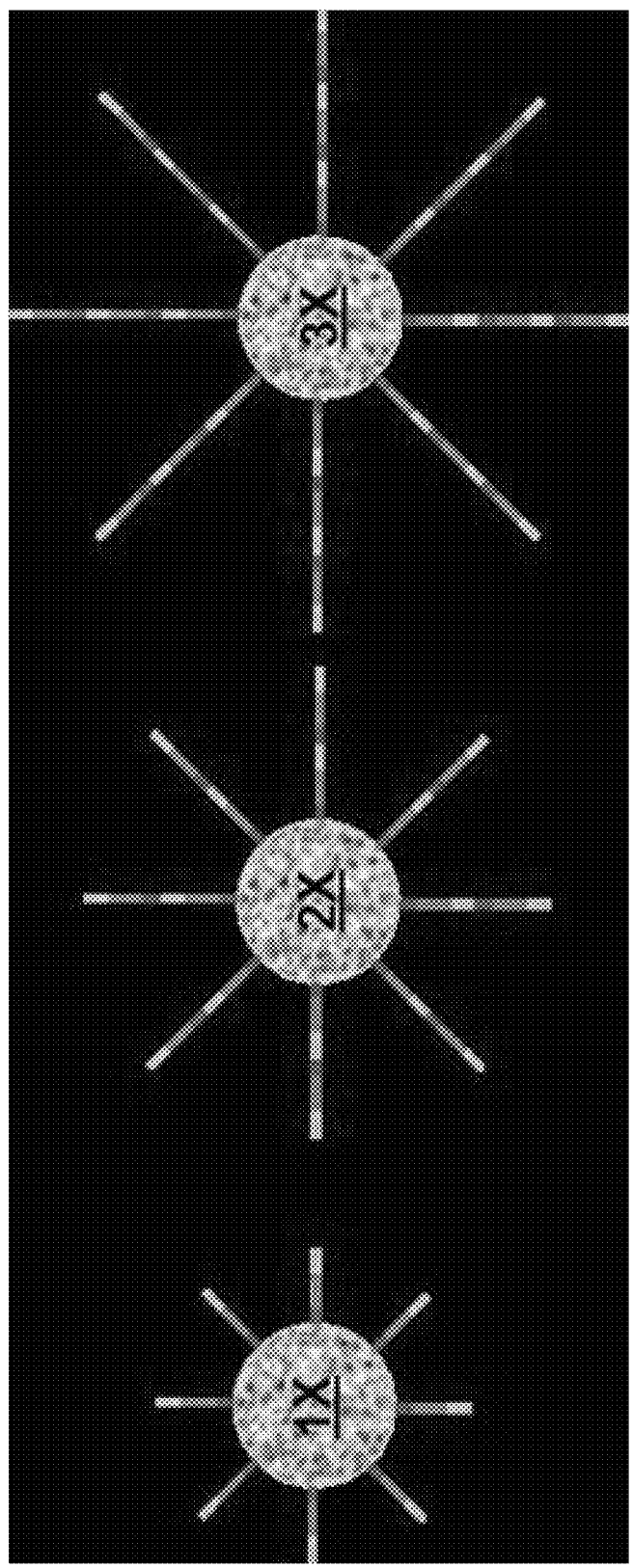
FIG. 3 is a simplified graphical representation of one embodiment of a result of the amplification strategy of FIG. 2 that comprise immobilized concatamers copies of a template species.

FIG. 3 provides an illustrative example, of the products of multiple rounds of denaturation and extension the can produce immobilized concatamer products having 2× and 3× the number of original immobilized copies, although it will be appreciated that greater than 3× concatamers are possible.

EXAMPLES

Concatamer PCR on 20 μm Beads

Standard emulsion creation, breaking and enriching procedures were employed
Reaction conditions

| Reagent | Concentration | |
| --- | --- | --- |
| Tris-Sulfate | 39 | mM |
| (NH$_4$)$_2$SO$_4$ | 11.7 | mM |
| MgSO$_4$ | 2.55 | mM |
| total dNTP*** | 3.52 | mM |
| Tween ® 80 | 0.005 | % |
| BSA | 0.05 | % |
| DNA template | 0.04 | uM |
| Standard PCR Primer | 5.87 | uM |
| Concatemer primer | 0.04 | uM |

-continued

| Reagent | Concentration | |
|---|---|---|
| Deep Vent Exo+ | 0.20 | U/uL |
| Ppiase | 0.03 | U/uL |

Thermocycler program: PCR_20
94 for 4 minutes
94 for 30 seconds
58 for 60 seconds
68 for 60 seconds
cycle 20 times
68 for 2 minutes
14 forever

```
MA2 primer and template set
ID Name Final oligo
A primer (seq primer) MA2
                                           (SEQ ID NO: 1)
CCCGCATAATCTCCCACTCc B primer on bead MMP3B
                                           (SEQ ID NO: 2)
CCTATCCCTGTGTGCCTTG
Concatemer primers (tested separately as
they would anneal to each other if used
together)

MApB2 primer
                                           (SEQ ID NO: 3)
GGAGTGGGAGATTATGCGGGCCTATCCCCTGTGTGCCTTG MBpA2 primer
                                           (SEQ ID NO: 4)
CAAGGCACACAGGGGATAGGCCCGCATAATCTCCCACTCC Template (A-100nt-B') MAB2 100nt
                                           (SEQ ID NO: 5)
CCCGCATAATCTCCCACTCcTCAGATGCCTAGTAAACAATGTTCGATCCG

GCGAAGTCTGCAAGAATCCAGCGCTGCCGGTTCGTCGGCGCTGTGCCGTG

GAGCTGACCTGATCGACGACTCGTCAAGGCACACAGGGGATAGG

MA3 primer and template set
A primer (seq primer) MA3
                                           (SEQ ID NO: 6)
CGCCCGTCTCTTTCTACCAc B primer on bead MMP3B
                                           (SEQ ID NO: 2)
CCTATCCCTGTGTGCCTTG
Concatemer primers (tested separately as
they would anneal to each other if used
together)

MApB3 primer
                                           (SEQ ID NO: 7)
GTGGTAGAAAGAGACGGGCGCCTATCCCCTGTGTGCCTTG MBpA3 primer
                                           (SEQ ID NO: 8)
CAAGGCACACAGGGGATAGGCGCCCGTCTCTTTCTACCAC Truncated Template (A-100nt-B')
                                           (SEQ ID NO: 9)
100ntCGCCCGTCTCTTTCTACCAcTCAGATGCCTAGTAAACAATGTTCG

ATCCGGCGAAGTCTGCAAGAATCCAGCGCTGCCGGTTCGTCGGCGCTGTG

CCGTGGAGCTGACCTGATCGACGACTCGTCAAGGCACACAGGGGATAGG
```

Figure 4:
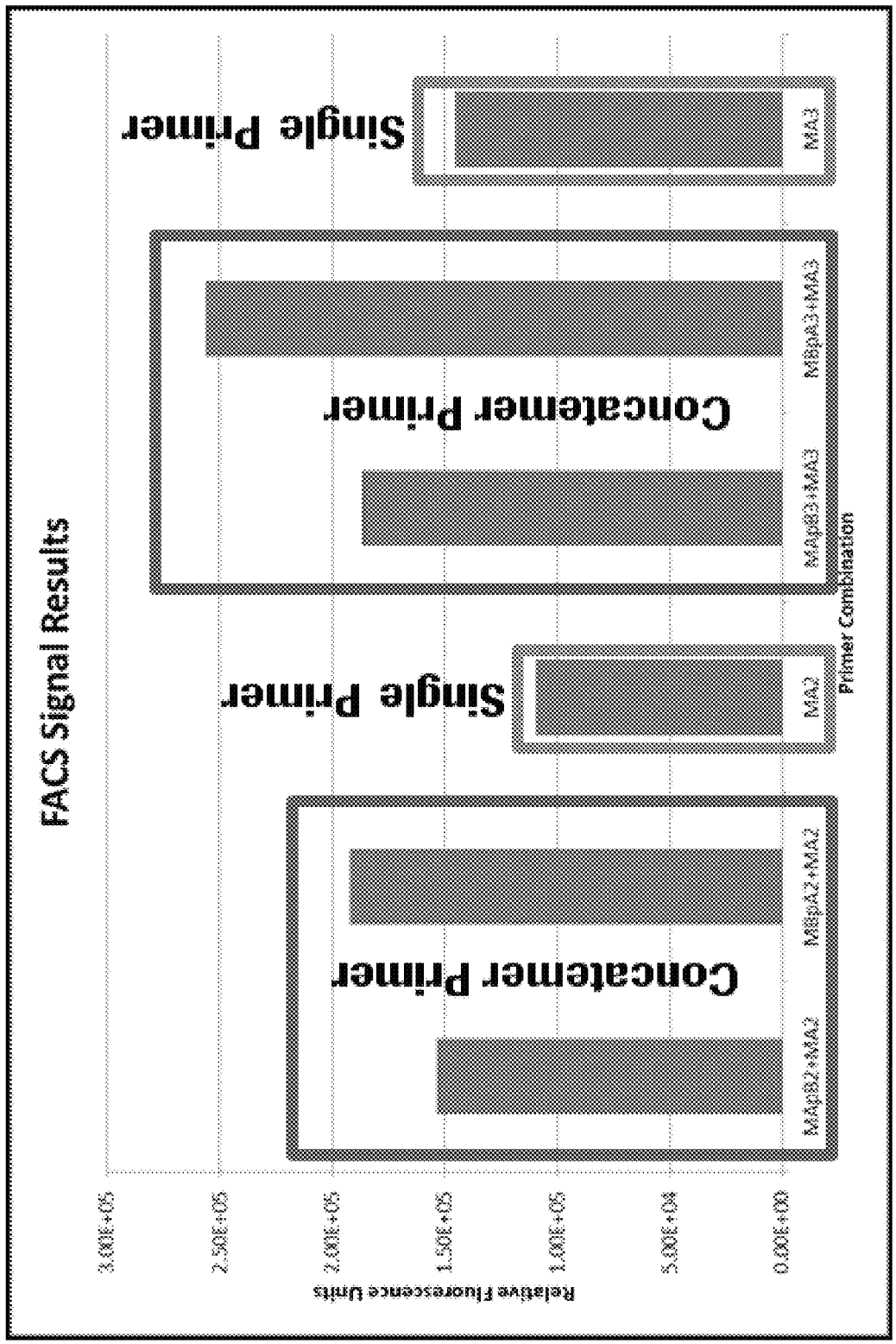
FIG. 4 is a simplified graphical representation of one embodiment of FACS analysis results of amplification products using a concatamer primer species versus single primer species.

The bead immobilized products were recovered and subjected to FACS analysis. A representation of analyzed signals are represented in FIG. 4 that show that when using concatemer primers, a higher signal is produced compared to standard primers are used alone. This is indicative of product concatenation. Additionally, in both cases the BpA primers produce higher signal than the ApB.

Figure 5:
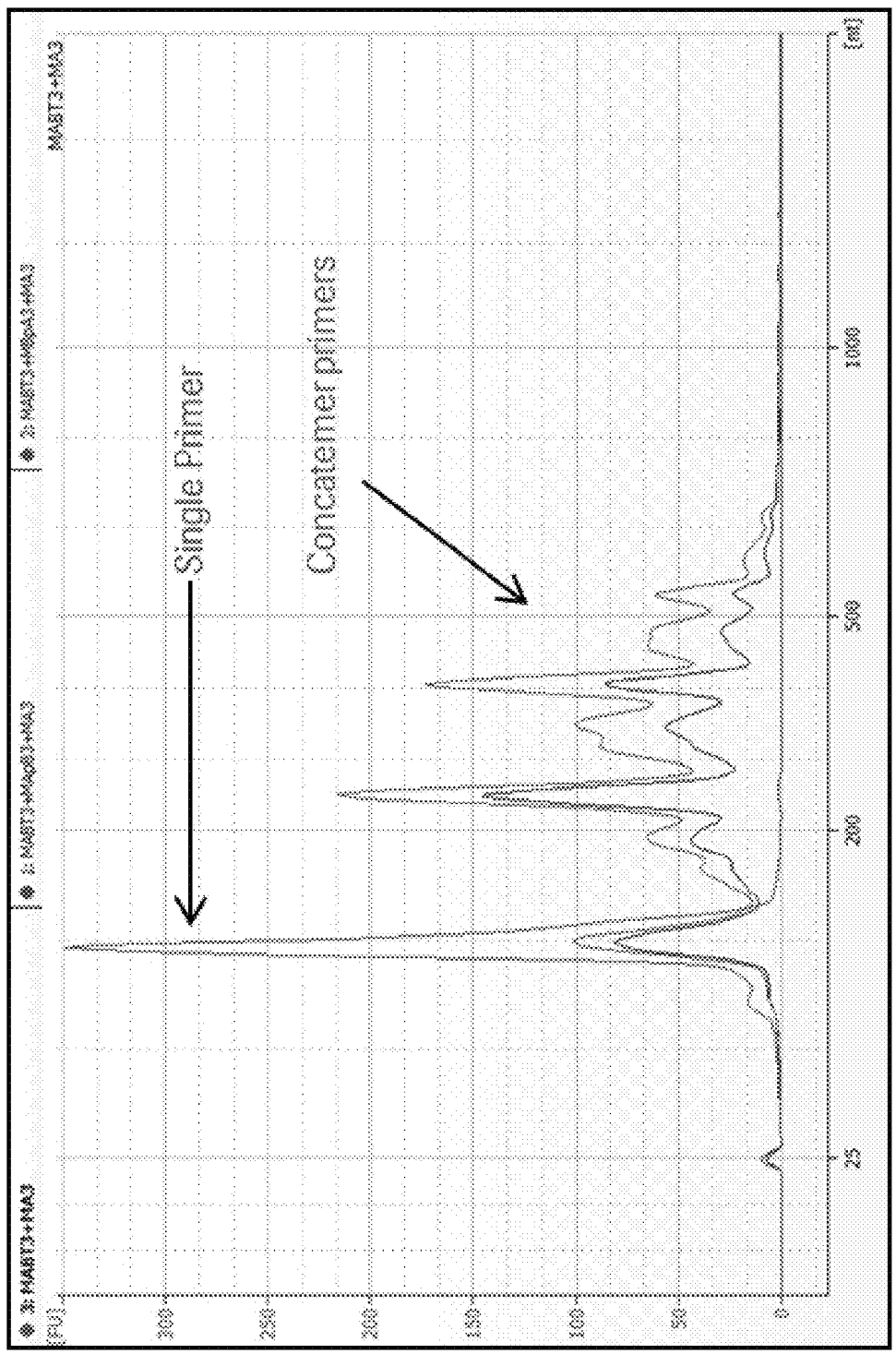
FIG. 5 is a simplified graphical representation of one embodiment of analysis results of amplification products using a concatamer primer species versus single primer species illustrating a difference in size distribution of the products.
Figure 6:
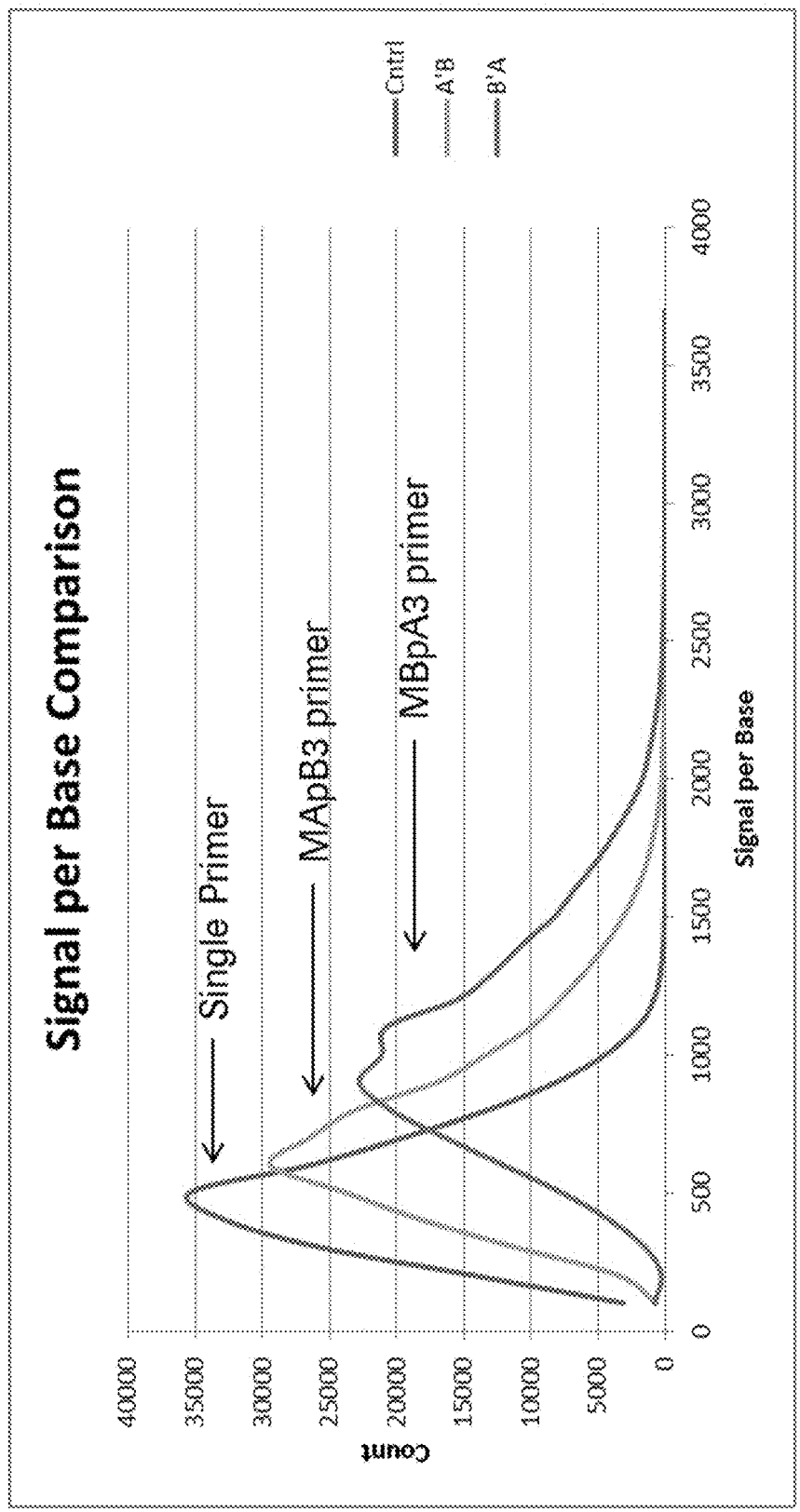
FIG. 6 is a simplified graphical representation of one embodiment of analysis results of amplification products using a concatamer primer species versus single primer species illustrating a difference in signal per base in a sequencing analysis.

Further, as illustrated in FIG. 5, the use of concatemer primers results in multiple size products while the single standard primer results in a single defined peak. When sequenced, the signal per base is higher when using concatamer primers when compared to the single standard primer alone as illustrated in FIG. 6.

Figure 7B:
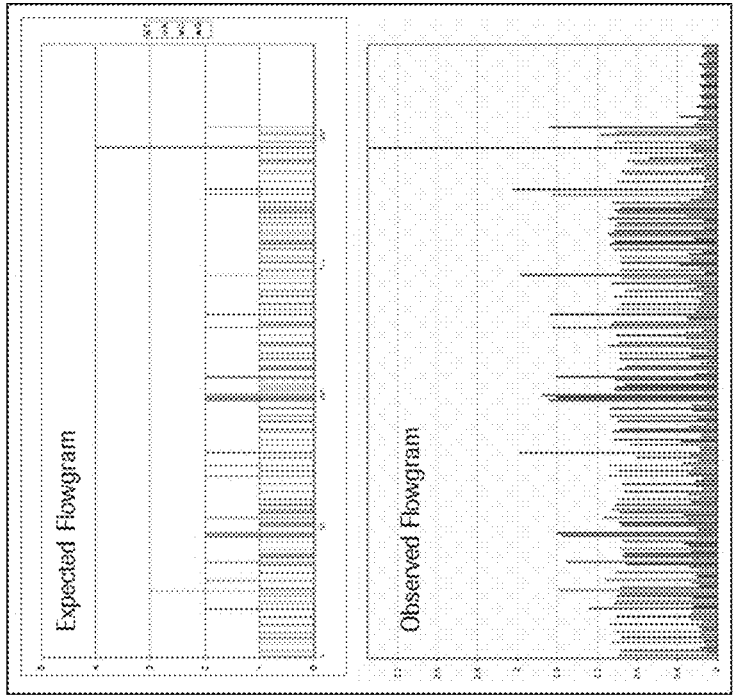
FIGS. 7A and 7B are simplified graphical representations of one embodiment of analysis results of amplification products using a concatamer primer species versus single primer species illustrating a difference in sequencing flowgrams.
Figure 7A:
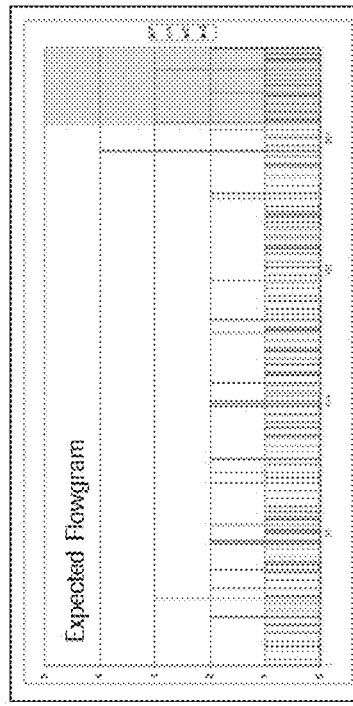

In addition, as the sequencing flowgram in FIG. 7A illustrates, the results on a GS-FLX instrument shows that the concatamer reaction produces a sequencing pattern that matches the expected flowgram. When the reaction begins to strand displace the next sequencing primer, signals and patterns start to weaken as expected due to the double stranded nature of the structure and because not all strands will have a second concatemer copy. Whereas, as expected, single primer standard PCR does not produce a flowgram after the initial template is sequenced as illustrated in FIG. 7B.

Concatamer PCR on ~1.4 μm Beads

Another challenge was amplifying enough templates onto a smaller capture bead (∥1.4 μm) to enable sequencing. Subsequently, evaluation of concatemer PCR onto a small ~1.4 μm capture bead was explored.

The experiment was non-emulsion solid phase amplification to determine feasibility of amplification of the concatamer product onto a smaller capture bead. PCR conditions evaluated listed in Table 1. Post thermocycling, the beads underwent melt assay, where PCR product not bound to the capture beads could be collected, purified, and run on a gel. The PCR product bound to the capture beads post clean-up would be annealed with a FAM complementary primer and run on a flow cytometer.

TABLE 1

List of PCR reactions tested.

| Capture Beads | Samples |
|---|---|
| ~1.4 μm bead | 1) MABT3 + MApB + MA3 |
| ~1.4 μm bead | 2) MABT3 + MBpA + MA3 |
| ~1.4 μm bead | 3) MABT3 + MA3 |

Figure 8:
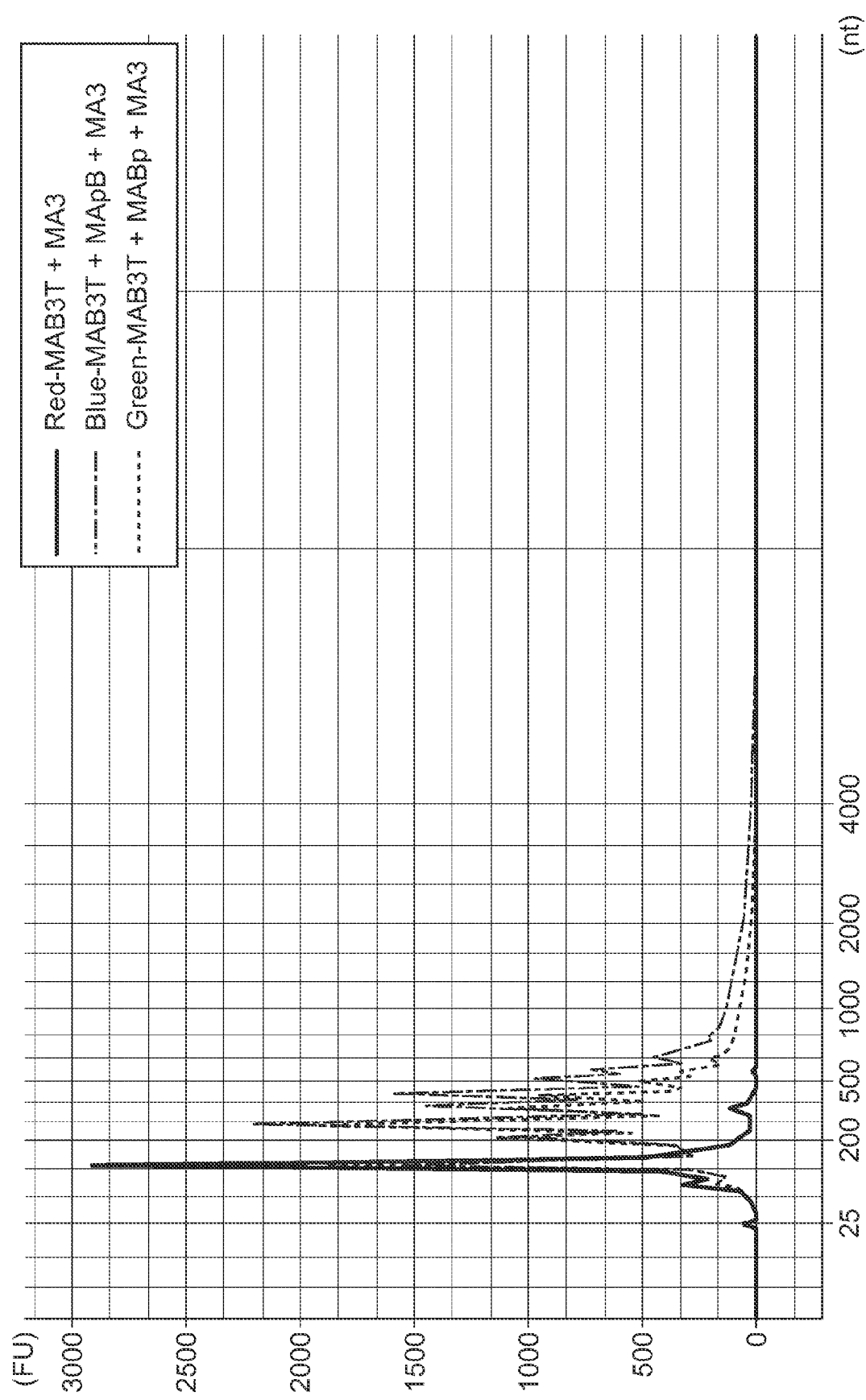
FIG. 8 is a simplified graphical representation of one embodiment of analysis results of amplification products using a concatamer primer species on a ~1.4 μm capture bead.

Concatamer products purified from the melt assay were run on an Agilent Bioanalyzer and the electropherogram, illustrated in FIG. 8, shows that concatenation occurred when MApB or MABp concatemer primers were used When, only the solution primer was used, peak was observed ∥148 bp, the length of the MABT3 template.

Figure 9:
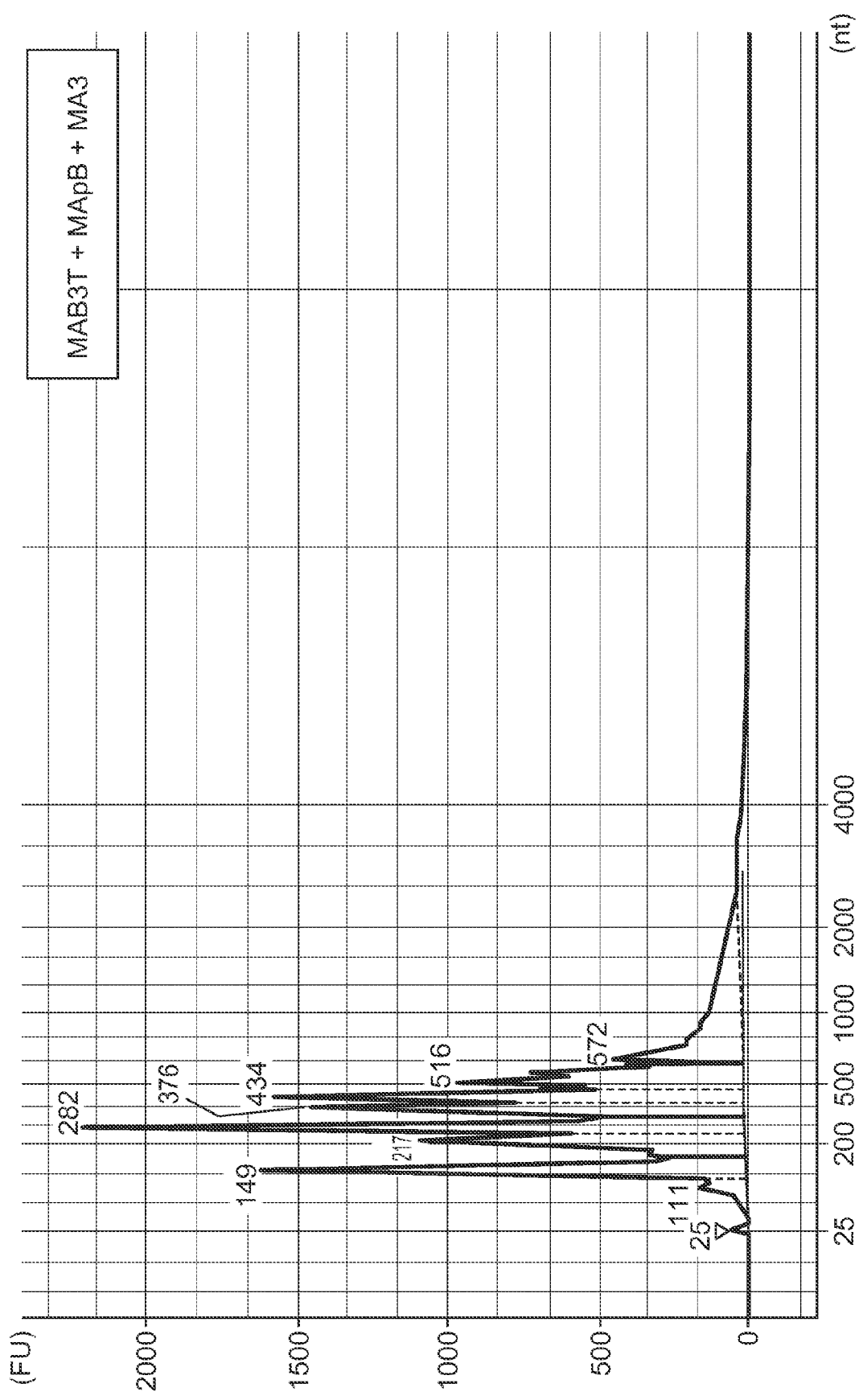
FIG. 9 is a simplified graphical representation of another embodiment of analysis results of amplification products using a concatamer primer species on a ~1.4 μm capture bead.

In instances whether MApB or MBpA concatemer primers were used, main peak height observed were ~148 bp intervals similar to what was observed for 20 μm capture bead, as illustrated in FIG. 9.

The fluorescence was measured with a BD Accuri™ C6 Flow Cytometer on beads amplified with either concatemer primers when compared to PCR reaction with just solution primer showed increase in fluorescence Table 2. This suggested with same number of PCR cycles, PCR reactions with concatemer primers yielded more product.

TABLE 2

Median fluorescence observed for PCR reactions with and without concatamer primers. Fluorescence was normalized to PCR reaction without concatamer primers.

| Plot 4: Multiple Samples Gated on R1 | Median FL1-A | Normalized to solution primer |
|---|---|---|
| A04 JSR MAB3T + MApB + MA3: This Plot | 5,391.00 | 1.50 |
| A05 JSR MAB3T + MABp + MA3: This Plot | 4,518.00 | 1.26 |
| A06 JSR MAB3T + MA3: This Plot | 3,600.00 | 1 |

Non-emulsion based solid phase amplification PCR reagents Reaction conditions

| Reagent | Concentration | |
|---|---|---|
| Tris-Sulfate | 39 | mM |
| $(NH_4)_2SO_4$ | 11.7 | mM |
| $MgSO_4$ | 2.55 | mM |
| total dNTP | 3.52 | mM |
| Tween 80 | 0.005 | % |
| BSA | 0.05 | % |
| DNA template | 0.08 | uM |
| Standard PCR Primer | 5.87 | uM |
| Concatamer Primer | 0.04 | uM |
| Deep Vent Exo+ | 0.38 | U/uL |
| PPiase | 2.5 | U/uL |

| Steps | Temperature and Time |
|---|---|
| 1 | 94° C. for 4 minutes |
| 2 | 94° C. for 30 seconds |
| 3 | 58° C. for 60 seconds |
| 4 | 68° C. for 60 seconds |
| 5 | cycle steps 2-4 nineteen times |
| 6 | 68 for 2 minutes |
| 7 | 14 forever |

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiments.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

What is claimed is:

1. A method for generating a population of amplified concatamer products, comprising:
   amplifying a template nucleic acid molecule using a first nucleic acid primer immobilized on a solid phase substrate and a second nucleic acid primer in solution to generate a population of substantially identical copies of the template nucleic acid molecule immobilized on the solid phase substrate;
   amplifying the population of substantially identical copies of the template nucleic acid molecule using a concatamer primer that comprises a first region complementary to a sequence of an end region of the population of substantially identical copies of the template nucleic acid molecule and a second region to generate a population of immobilized concatamer products of the substantially identical copies of the template nucleic acid molecule.

2. The method of claim 1, wherein,
   each of the population of immobilized concatamer products comprise three or more concatamer copies of one of the substantially identical copies of the template nucleic acid molecule.

3. The method of claim 1, wherein,
   the end region of the population of substantially identical copies of the template nucleic acid molecule comprises an adaptor sequence.

4. The method of claim 1, wherein,
   the second region of the concatamer primer is complementary to the first nucleic acid primer immobilized on the solid phase substrate.

5. The method of claim 1, wherein,
   the solid phase substrate which is fabricated from a material selected from the group consisting of cellulose, a cellulose derivative, an acrylic resin, glass, a silica gel, polystyrene, gelatin, polyvinyl pyrrolidone, a co-polymer of vinyl and acrylamide, a polystyrene cross-linked with divinylbenzene, polyacrylamide, a latex gel, polystyrene, dextran, rubber, silicon, a plastic, nitrocellulose, a natural sponge, a silica gel, control pore glass, a metal, a cross-linked dextran, and agarose gel.

6. The method of claim 1, wherein, the template nucleic acid molecule has a length of up to 1000 nucleic acid residues.

7. The method of claim 1, wherein, the template nucleic acid molecule comprises one or more additional functional elements selected from the group consisting of a primer sequence for amplification or sequencing methods, a quality control element, an adapter element, and a unique identifier.

8. The method of claim 7, wherein, the unique identifier is a multiplex identifier (MID).

9. The method of claim 8, wherein, the MID identifies a feature of a sample, wherein the feature is an experimental condition, a treatment, a species, an individual subject, a tissue type, or a cell type.

10. The method of claim 9, wherein, the template nucleic acid molecule comprises more than one MID.

11. The method of claim 9, wherein, a position of the MID in the template nucleic acid molecule is known relative to a feature of the template nucleic acid molecule or to an adaptor element coupled to the template molecule.

12. The method of claim 11, wherein, the feature of the template nucleic acid molecule is a specific nucleic acid residue in the molecule, a recognizable sequence marker, or one or more primer elements.

13. The method of claim 12, wherein the recognizable sequence marker is a Key element.

14. The method of claim 13, wherein, the Key element or the one or more primer elements each has a known sequence composition.

15. The method of claim 1, wherein, amplifying the population of substantially identical copies of the template nucleic acid molecule using a concatamer primer occurs via polymerase chain reaction (PCR) or emulsion PCR (emPCR).

16. The method of claim 1, wherein, the solid phase substrate is a bead.

17. The method of claim 16, wherein, the bead has a diameter of between about 1.4 μm and about 20 μm.

18. The method of claim 1, wherein, the solid phase substrate is a planar substrate selected from the group consisting of a slide type substrate, a semiconductor chip comprising well type structures, a microwell array, a waveguide type reaction substrate, and a PTP array.

* * * * *

UNITED STATES PATENT AND TRADEMARK OFFICE
CERTIFICATE OF CORRECTION

PATENT NO.        : 9,624,519 B2                                           Page 1 of 1
APPLICATION NO.   : 14/466063
DATED             : April 18, 2017
INVENTOR(S)       : Godwin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
cccgcataat ctcccactcc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
cctatcccct gtgtgccttg                                               20

<210> SEQ ID NO 3
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 3
ggagtgggag attatgcggg cctatcccct gtgtgccttg                         40
```

```
<210> SEQ ID NO 4
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 4
caaggcacac aggggatagg cccgcataat ctcccactcc                          40

<210> SEQ ID NO 5
<211> LENGTH: 143
<212> TYPE: DNA
<213> ORGANISM: Artificial Sequence
<220> FEATURE:
<223> OTHER INFORMATION: Synthetic polynucleotide

<400> SEQUENCE: 5
ccgcataatc tcccactcct cagatgccta gtaaacaatg ttcgatccgg cgaagtctgc    60
aagaatccag cgctgccggt tcgtcggcgc tgtgccgtgg agctgacctg atcgacgact   120
cgtcaaggca cacaggggat agg                                           143

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
cgcccgtctc tttctaccac                                                20

<210> SEQ ID NO 7
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 7
gtggtagaaa gagacgggcg cctatcccct gtgtgccttg                          40

<210> SEQ ID NO 8
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 8
caaggcacac aggggatagg cgcccgtctc tttctaccac                          40

<210> SEQ ID NO 9
<211> LENGTH: 144
<212> TYPE: DNA
<213> ORGANISM: Artificial Sequence
<220> FEATURE:
<223> OTHER INFORMATION: Synthetic polynucleotide

<400> SEQUENCE: 9
cgcccgtctc tttctaccac tcagatgcct agtaaacaat gttcgatccg gcgaagtctg    60
caagaatcca gcgctgccgg ttcgtcggcg ctgtgccgtg gagctgacct gatcgacgac   120
tcgtcaaggc acacagggga tagg                                          144
```

<210> SEQ ID NO 10
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 10
aggtatgggt tggtgagtgg aaagacgcct gccctcctta ctac         44

<210> SEQ ID NO 11
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 11
tgcggacggg aggaatgatg agtctacgga tcatttgtta caagctaggc cgcttcagac      60
gttcttaggt cgcgacggcc aagcagccgc gacacggcac ctcgactgga ctagctgctg     120
agcatccata cccaaccact cacctttc                                        148

<210> SEQ ID NO 12
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 12
aggtatgggt tggtgagtgg aaagacgcct gccctcctta ctactcagat gcctagtaaa      60
caatgttcga tccggcgaag tctgcaagaa tccagcgctg ccggttcgtc ggcgctgtgc     120
cgtggagctg acctgatcga cgactcgtag gtatgggttg gtgagtggaa ag            172

<210> SEQ ID NO 13
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 13
tccataccca accactcacc tttctgcgga cggaggaat gatgagtcta cggatcattt      60
gttacaagct aggccgcttc agacgttctt aggtcgcgac ggccaagcag ccgcgacacg    120
gcacctcgac tggactagct gctgagcatc catacccaac cactcacctt tc            172

<210> SEQ ID NO 14
<211> LENGTH: 172
<212> TYPE: DNA
<213> ORGANISM: Artificial Sequence
<220> FEATURE:
<223> OTHER INFORMATION: Synthetic polynucleotide

<400> SEQUENCE: 14
aggtatgggt tggtgagtgg aaagacgcct gccctcctta ctactcagat gcctagtaaa      60
caatgttcga tccggcgaag tctgcaagaa tccagcgctg ccggttcgtc ggcgctgtgc     120
cgtggagctg acctgatcga cgactcgtag gtatgggttg gtgagtggaa ag            172

<210> SEQ ID NO 15
<211> LENGTH: 172

```
<212> TYPE: DNA
<213> ORGANISM: Artificial Sequence
<220> FEATURE:
<223> OTHER INFORMATION: Synthetic polynucleotide

<400> SEQUENCE: 15
tccataccca accactcacc tttctgcgga cgggaggaat gatgagtcta cggatcattt      60
gttacaagct aggccgcttc agacgttctt aggtcgcgac ggccaagcag ccgcgacacg     120
gcacctcgac tggactagct gctgagcatc catacccaac cactcacctt tc             172

<210> SEQ ID NO 16
<211> LENGTH: 320
<212> TYPE: DNA
<213> ORGANISM: Artificial Sequence
<220> FEATURE:
<223> OTHER INFORMATION: Synthetic polynucleotide

<400> SEQUENCE: 16
aggtatgggt tggtgagtgg aaagacgcct gccctcctta ctactcagat gcctagtaaa      60
caatgttcga tccggcgaag tctgcaagaa tccagcgctg ccggttcgtc ggcgctgtgc     120
cgtggagctg acctgatcga cgactcgtag gtatgggttg gtgagtggaa agacgcctgc     180
cctccttact actcagatgc ctagtaaaca atgttcgatc cggcgaagtc tgcaagaatc     240
cagcgctgcc ggttcgtcgg cgctgtgccg tggagctgac ctgatcgacg actcgtaggt     300
atgggttggt gagtggaaag                                                 320

<210> SEQ ID NO 17
<211> LENGTH: 320
<212> TYPE: DNA
<213> ORGANISM: Artificial Sequence
<220> FEATURE:
<223> OTHER INFORMATION: Synthetic polynucleotide

<400> SEQUENCE: 17
tccataccca accactcacc tttctgcgga cgggaggaat gatgagtcta cggatcattt      60
gttacaagct aggccgcttc agacgttctt aggtcgcgac ggccaagcag ccgcgacacg     120
gcacctcgac tggactagct gctgagcatc catacccaac cactcacctt tctgcggacg     180
ggaggaatga tgagtctacg gatcatttgt tacaagctag gccgcttcag acgttcttag     240
gtcgcgacgg ccaagcagcc gcgacacggc acctcgactg gactagctgc tgagcatcca     300
tacccaacca ctcaccttc                                                  320
```